United States Patent [19]

Howard, III et al.

[11] Patent Number: 5,408,535
[45] Date of Patent: Apr. 18, 1995

[54] VIDEO TEST STRIP READER AND METHOD FOR EVALUATING TEST STRIPS

[75] Inventors: Willis E. Howard, III, Elkhart; Dijia Huang, Granger; Robert W. Rogers; Gerald H. Shaffer, both of Elkhart; Mark A. Yoder, Bristol, all of Ind.

[73] Assignee: Miles Inc., Elkhart, Ind.

[21] Appl. No.: 117,782

[22] Filed: Sep. 7, 1993

[51] Int. Cl.[6] .......................... G06K 9/00; G01N 21/01
[52] U.S. Cl. .................................. 382/1; 382/6; 382/61; 436/43; 422/82.05; 356/421
[58] Field of Search ................. 382/1, 8, 17, 61, 6; 364/526, 413.11; 422/58, 65, 66, 67, 87, 85, 82.05, 91; 436/44, 46, 47, 48, 43; 356/402, 408, 421; 250/226, 561

[56] References Cited

U.S. PATENT DOCUMENTS

| | | | |
|---|---|---|---|
| 3,486,179 | 12/1969 | Beutler et al. | 470/19 |
| 3,705,504 | 12/1972 | Johnson | 70/93 |
| 3,825,056 | 7/1974 | Grosko et al. | 164/426 |
| 4,230,540 | 10/1990 | Archer et al. | 204/67 |
| 4,648,048 | 3/1987 | Dorn et al. | 364/526 |
| 4,798,703 | 1/1989 | Minekane | 427/65 |
| 4,817,785 | 4/1989 | Farber | 198/803.01 |
| 4,867,946 | 9/1989 | Gross et al. | 422/58 |
| 5,055,261 | 10/1991 | Khoja et al. | 422/82.05 |
| 5,143,694 | 9/1992 | Shäfer et al. | 422/65 |
| 5,181,257 | 1/1993 | Steiner et al. | 382/17 |
| 5,290,701 | 3/1994 | Wilkins | 382/6 |

Primary Examiner—Leo H. Boudreau
Assistant Examiner—Larry Prikockis
Attorney, Agent, or Firm—Roger N. Coe

[57] ABSTRACT

A video test strip reader uses a video imager or camera for viewing a viewing field containing reagent test strips each having test pads reacted with a specimen containing constituents of interest. The video imager produces an analog signal representing an image of the viewing field. An image handler coupled to the video imager converts or digitizes the analog signal into a digital signal representing the image and stores the image in the form of an array of pixels representing the image. Each pixel contains color information broken down into red, green or blue (RGB). A processor coupled to the image handler analyzes the array of pixels, determines the location and orientation of a test strip, identifies the test areas on the test strip, measures the corresponding test areas on the strip at the proper times and calculates the test results, such as the concentration of the constituents of interest in the specimen or other measurable properties of the specimen such as color or specific gravity, etc. Accordingly, the video test strip reader can simultaneously locate, color analyze and time track multiple test strips on the viewing field.

59 Claims, 9 Drawing Sheets

VIDEO TEST STRIP READER AND METHOD FOR EVALUATING TEST STRIPS

FIELD OF THE INVENTION

The present invention generally relates to the field of clinical chemistry. More particularly, the present invention relates to a visual imaging system that analyzes the color change associated with one or more test areas on a test strip following contact thereof with a liquid specimen, such as urine or blood.

BACKGROUND OF THE INVENTION

Reagent test strips are widely used in the field of clinical chemistry. A test strip usually has one or more test areas, and each test area is capable of undergoing a color change in response to contact with a liquid specimen. The liquid specimen usually contains one or more constituents or properties of interest. The presence and concentrations of these constituents of interest in the specimen are determinable by an analysis of the color changes undergone by the test strip. Usually, this analysis involves a color comparison between the test area or test pad and a color standard or scale. In this way, reagent test strips assist physicians in diagnosing the existence of diseases and other health problems.

Color comparisons made with the naked eye can lead to imprecise measurement. Today, strip reading instruments exist that employ reflectance photometry for reading test strip color changes. These instruments accurately determine the color change of a test strip within a limited wavelength range or bandwidth but sometimes fail to measure minute color inconsistencies outside the limited bandwidth. For example, such an instrument can fail to detect traces of blood within a urine specimen on a MULTISTIX® reagent strip of the type sold by Miles Inc., Diagnostics Division, of Elkhart, Ind. 46515. After the urine specimen contacts the test pad of a MULTISTIX® reagent strip, intact blood cells appear as tiny green blotches on the yellow test area. Existing strip readers detect the overall color of the test pad but can ignore the small blotches of green. In addition, existing strip reading instruments using one or more wavelengths can lead to a false positive bilirubin result in the presence of interference from indoxyl sulfate. Visually, the atypical color is easily detected but not by prior strip readers that only analyze a limited bandwidth of the entire visual spectrum.

The first commercially available strip reading instruments of this type were effective but unable to adequately cope with the large numbers of specimens handled by clinical laboratories. These instruments require inserting a single test strip, reading the test strip and removing the test strip from the instrument before the instrument can analyze the next test strip. Moreover, with certain instruments the speed of operation is limited by the requirement of precise placement of the strip in the instrument.

Automation of strip reading instruments has significantly improved the speed with which specimens are processed. U.S. Pat. No. 5,055,261 discloses a multiple-strip reading instrument utilizing reflectance photometry to read test strips. An operator sequentially places the test strips transversely in a loading area. A blotter arm orients the test strips on rails extending from the loading area to one or more reading stations employing read heads and then to a waste receptacle.

This instrument provides for the reading of reagent strips with multiple test areas having varying incubation times. An indexing mechanism in timed relation with the blotter arm incrementally advances the strips in spaced parallel relation a predetermined distance along the rails. After each incremental advance, each test strip dwells for a predetermined time period in its new position. Consequently, individual test strips sequentially advance to a reading position where, during the dwell period, certain test areas are read. Subsequently, the instrument advances the test strip to the next reading position where the instrument reads the other test areas on the test strip with longer incubation times. This arrangement is somewhat inflexible to variations in incubation times for varying test strips because the timing of this instrument accounts for the distance that the test strip travels from the loading area to the read heads, the incubation times for a certain test area and the indexing rate of the indexing mechanism. Thus, if the instrument reads a test strip having test areas with different incubation times than the typical test strip, the instrument can obtain inaccurate results.

The instrument embodied in U.S. Pat. No. 5,143,694 also transports test strips at a right angle to their longitudinal direction from a strip loading area, along a transport path under the read heads to a waste receptacle. In order to obtain accurate results, these instruments require that the test strips be read at the appropriate time.

A common feature of these instruments is a visual and auditory prompt signalling the operator to dip a strip in the sample and place it in the loading area of the instrument. Typically, these prompts occur at fixed time intervals, such as every 10 or 12 seconds. Unfortunately, operators frequently fail to comply with the prompts by either not understanding or choosing to ignore the manufacturer's instruction about immersing the test strip when the tone is presented. This timing differential between the instrument prompt and when the operator actually dips the test strip can cause a degradation of measurement results. Moreover, forcing the user to dip and place strips as dictated by the instrument adds pressure onto the operator and can lead to human error.

SUMMARY OF THE INVENTION

The present invention efficiently provides enhanced reagent test strip measurement results, improves test strip reading efficiency, eliminates the inflexibility associated with prior reagent test strip readers and reduces the potential for human error degrading test results. The present invention accomplishes this by utilizing a color video imager or camera aimed at a viewing field containing reagent test strips. Each test strip has test pads reacted with a specimen containing constituents of interest. The video imager produces an analog signal representing an image of the viewing field. An image handler coupled to the video imager includes a signal converter that converts or digitizes the analog signal into a digital signal representing the image. Alternatively, the video imager can include the signal converter such that the video imager provides a digital signal representing the image to the image handler. The image handler stores the image, represented by the digital signal, in the form of an array of pixels representing the image. Each pixel contains color information broken down into red, green or blue (RGB). A processor coupled to the image handler analyzes the array of pixels, determines the location and orientation of a test strip and its test pads, measures the corresponding test areas or pads on the strip at the proper time and calculates the test results for the specimen. The present invention improves the efficiency of the strip reader by simultaneously analyzing and time tracking multiple test strips on the viewing field.

In a preferred embodiment of the present invention, the processor for the video strip reader detects the placement and removal of a test strip on the viewing field. Test strip placement occurs when an operator dips the test strip in a specimen and places the test strip on the viewing field. The processor detects the placement of a test strip onto the viewing field by detecting the test strip as having pixel values above a background threshold level. The processor also detects the removal from the viewing field of an existing test strip when the previous pixel values corresponding to the test strip have fallen below the background threshold level. If the operator adds a new test strip, the processor locates the test pads for the test strip by analyzing the pixel array and finding the boundaries of the test strip. The processor also tracks the amount of time that the test strip is on the viewing field. At the proper time, the processor analyzes the appropriate test areas or pads and calculates the test results, such as the concentrations of the constituents of interest.

In this way, the video reader of the present invention eliminates the potential degradation of measurement results due to human error, and, at the same time improves the efficiency of test strip reading. The operator is not required to comply with timed prompts from the test strip reader to dip a test strip in a specimen and immediately place the test strip on the loading area. The operator just dips the test strip in a specimen and immediately places the test strip in the viewing field of the present invention, prompting the machine to time and analyze each strip placed in the viewing field. Strip reading efficiency improves because the video reader, can analyze multiple test strips simultaneously, and the operator is also not constrained by the time prompts of previous strip readers.

In another embodiment of the present invention, a transport mechanism transports test strips from a loading area into the viewing field and into a waste receptacle. The processor of the video test strip reader itself or a separate loading area sensor detects the placement of a test strip on the loading area. Upon the placement of the test strip on the loading area, the processor tracks the timing for the corresponding test strip. In one embodiment, the placement of the test strip on the loading area triggers the transport mechanism to move the test strip in the viewing field. After entering the viewing field, the test strip does not move until another test strip is placed in the loading area. At that time, the transport mechanism moves or indexes the test strip a fixed distance in the viewing field. The test strips in the viewing field will move the same fixed distance with each subsequent index of another test strip. The transport mechanism indexes multiple test strips in the viewing field and, thereby, maximizes the number of test strips in the viewing field and improves the efficiency of the test strip reader. The present invention also encompasses a test strip reader where the processor controls the movement of the transport mechanism according to the timing of the various test strips in the viewing field.

The video test strip reader of the present invention permits enhanced test strip reading capabilities because of its video imaging capabilities. For example, the present invention can utilize markings incorporated on each test strip to distinguish between individual test strips or between different types of test strips. The present invention can also utilize a color standard contained in the viewing field, providing an absolute reflectance standard for the processor. Furthermore, the present invention has a wavelength response similar to the human eye and uses the entire visual spectrum to view the viewing field. In contrast to prior optical instruments employing reflectance photometry within a limited bandwidth, the video test strip reader can detect small spots or other color distortions on a test pad, such as the green spots representing intact blood cells in a urine specimen and the color distortion in a bilirubin test that signals a false positive bilirubin result.

In addition, the present invention is capable of measuring test strips whose format does not conform to that of a MULTISTIX® reagent strip. Certain immunodiagnostic strips are constructed such that the presence of an analyte in the sample produces a narrow band of color across the width of the strip. The presence of multiple analytes would be indicated by the development of colored bands at different locations along the length of the strip. Certain other immunodiagnostic strips may consist of adjacent pads with no physical separation between them. In contrast to prior optical instruments which require a fixed test pad size and fixed spacing between test pad areas, the video test strip reader can locate each band of color, determine the physical extent of each color band and measure spectral reflectance within each color band.

Thus, the present invention provides enhanced, efficient and flexible reading of different test strips while reducing the risk of human error. The present invention accomplishes this by utilizing a video imaging system to perform test strip measurement on test pads located by the processor. The video strip reader operates similar to the human eye and provides enhanced detection because the entire visual spectrum is analyzed. In addition, the visual reader can simultaneously time and analyze multiple test strips, improving efficiency and flexibility. Flexibility is further improved because the timing for the present invention does not rely on the fixed mechanical structure of the test strip reader itself.

BRIEF DESCRIPTION OF THE DRAWINGS

The advantages of the present invention will become apparent upon reading the following detailed description and upon reference to the accompanying drawings in which.

DETAILED DESCRIPTION OF THE PREFERRED EMBODIMENTS

Figure 1:
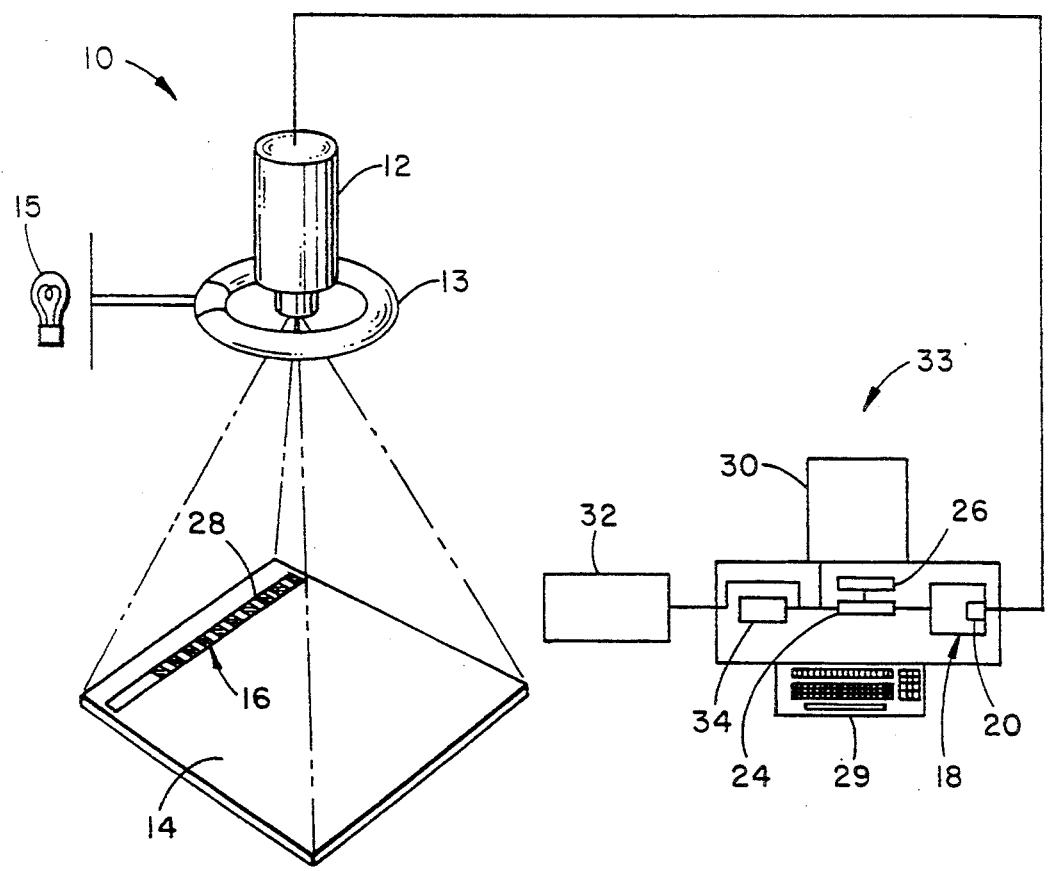
FIG. 1 shows an embodiment of the visual test strip reader in accordance with the present invention.

Referring now to the drawings, and more particularly to FIG. 1, there is illustrated a video test strip reader in accordance with the present invention, generally designated by the reference numeral 10. The video reader 10 provides enhanced measurement results, eliminates the inflexibility associated with prior reagent test strip readers and reduces the potential for human error degrading test results. Moreover, the video strip reader 10 improves the efficiency of the strip reader because the present invention can simultaneously locate, color analyze and time track multiple test strips on the viewing field. The video strip reader 10 utilizes a color video imager 12 or camera that views a reading field 14 containing a reagent test strip 16. Each test strip 16 has test pads 28 reacted with a specimen containing constituents of interest. The test pads 28 change color when reacted with a liquid specimen containing constituents of interest. By analyzing the color of a test pad 28 after one or more read times for the test pad 28 have expired, the concentration or presence of a constituent of interest can be determined as well as other measurable properties of the liquid specimen such as color or specific gravity.

The video imager 12 produces an analog signal representing a color image of the viewing field 14. An example of the video imager 12 is a Model WAT-201 color video camera sold by Watec Co., Ltd. The present invention also encompasses using as the video imager a CID (charge injection device), a monochrome CCD camera having external color filters or a vidicon camera. An illumination source 13 illuminates the viewing field 14. The illumination source 13 should evenly illuminate the viewing field 14 in order for video imager 12 to accurately measure the color or reflectance of the various test pads 28. The illumination source 13 is preferably a DC light source with a control feedback to minimize light fluctuations. This illumination source 13 is shown in FIG. 1 as a fiber optic illumination ring connected to a stabilized source 15. Alternatively, a lamp positioned in place of illumination source 13 can be used.

The video test strip reader 10 of FIG. 1 is illustrated with a conventional personal computer 33. The personal computer includes an image handler 18 conventionally coupled to the video imager 12. The image handler 18 includes a signal converter 20 that converts or digitizes the analog signal from the video imager 12 into a digital signal representing the image. The image handler 18 also stores the image represented by the digital signal in the form of a two-dimensional array or matrix of pixels. The image handler 18 is a commercial frame-grabber board coupled to an I/O port of the personal computer 33. Typically, commercial frame-grabber boards include a signal converter 20 for converting the analog signal from the video imager 12 to a digital signal. Accordingly, FIG. 1 illustrates the image handler 18 as including the signal converter 20, but the signal converter 20 can be separate from the image handler 18. The image handler 18 can be a MVPAT frame-grabber board sold by Matrox.

The personal computer 33 includes a processor 24 and storage memory 26. The processor 24, conventionally coupled to the image handler 18, initially calibrates and produces reflectance reference matrices for the video strip reader 10 by reading the reflectance values for the viewing field 14. The processor 24 then analyzes successive arrays of pixels to determine the placement of the test strip 16 on the viewing field 14 and, with a timing mechanism (not shown), keeps track of an elapsed time from the placement of the corresponding test strip 16 on the viewing field 14. The timing mechanism of the processor 24 can include a system clock running at a known frequency. After the placement of a test strip 16 on the viewing field 14, the processor 24 determines the location and orientation of the test strip 16 and its test pads 28 from a current array of pixels. When the elapsed time for a test strip 16 exceeds the read time or incubation time for a test pad 28 on that test strip 16, the processor 24 measures the reflectance for that test area or test pad 28. When multiple read times are used, the previous step is repeated for each read time. The processor 24 then calculates the concentration of the constituents of interest in the specimen or other test results using the reflectance reference matrices and the reflectance values for those portions of the array of pixels representing the test pads 28. At this point, the test strip 16 is finished. The processor 24 is conventionally coupled to a display 30 or a printing mechanism 32 for displaying the test results. The processor 24 is also coupled to a storage memory 26 for storing analysis data, instructions and calculation results. The personal computer 33 is an IBM AT personal computer with a 286 microprocessor or compatible shown with the display 30, the printing mechanism 32, a secondary storage 34, such as disk storage, and a keyboard 29.

Figure 2:
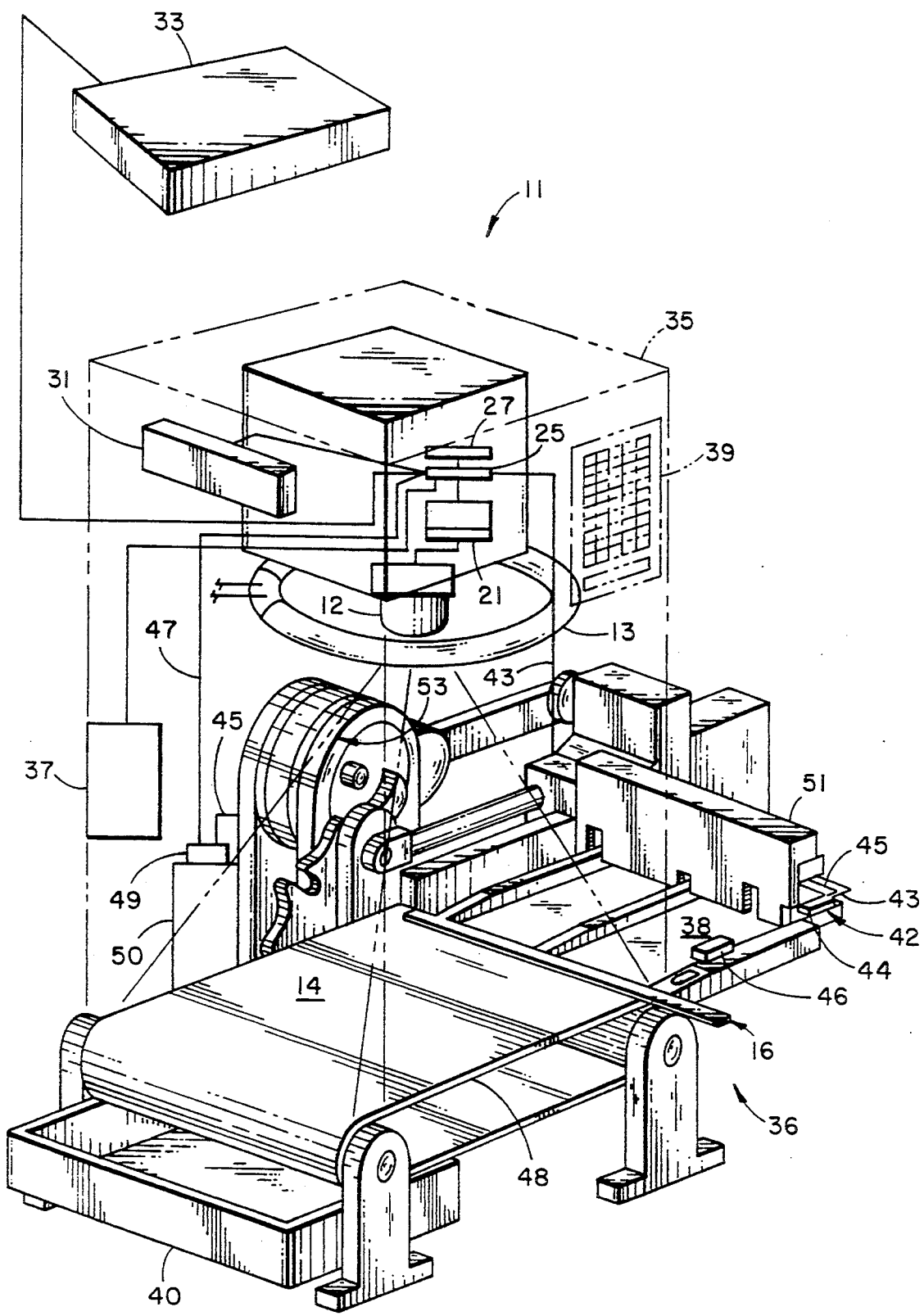
FIG. 2 shows an alternative embodiment of the video test strip reader in accordance with the present invention.

FIG. 2 illustrates another video strip reader in accordance with the present invention, generally designated by the reference numeral 11. Video reader 11 also includes a video imager 12, an image handler 19, a processor 25 and storage memory 27 that operate as the corresponding elements shown in FIG. 1, but the embodiment of FIG. 2 shows these elements as being together within a housing 35 of the video test strip reader 11. The housing 35 prevents outside interference from adversely affecting test strip analysis. The processor 25 can be a DSP (digital signal processor) on a dedicated board along with storage memory 27. The image handler 19 can be a separate frame grabber board or a custom frame-grabber on the same or a different dedicated board. As stated above, the image handler 19 is described as including a signal converter 21. The signal converter 21 can be a conventional video analog to digital converter. Alternatively, the processor 25, the image handler 19 and the storage memory 27 can take the form of hard-wired circuitry. As in FIG. 1, FIG. 2 shows an illumination source 13 shining on the viewing field 14 with a test strip 16. The processor 25 is also shown as being coupled to a secondary storage, a display 31, a printer 33, and a key pad 39.

In FIG. 2, the video strip reader 11 uses a transport mechanism 36 to transport the test strip 16 from a loading area 38 into the viewing field 14 and into a waste receptacle 40. Although the loading area 38 is not shown as being in the viewing field 14 in FIG. 2, placement of the loading area 38 can be alternatively positioned within the viewing field 14. If the loading area 38 is in the viewing field 14, the test strip reader 11 can detect the placement of a test strip 16 onto the viewing field 14 by utilizing the processor 25 to analyze a current pixel array representing an image of the viewing field 14. Upon detecting the placement of a test strip 16 on the viewing field 14, the processor 25, which includes a known timing mechanism (not shown), keeps track of an elapsed time from the placement of the corresponding test strip 16 on the viewing field 14. The timing mechanism of the processor 25 can include a system clock running at a known frequency. In the embodiment where the processor 25 detects the placement of the test strip 16 on the loading area in the viewing field 14, the processor 25 is coupled to and signals the transport mechanism 36 to transport the test strip 16. Additionally, the processor 25 can control the movement of the transport mechanism 36 according to the status of the various test strips 16 on the viewing field 14. For example, if all the test strips 16 are finished, the processor 25 can signal the transport mechanism 36 to transport the test strips 16 to the waste receptacle 40.

If the loading area 38 is not within the viewing field 14 as in FIG. 2, then a loading sensor 42 detects the placement of the test strip 16 on the loading area 38 and signals the processor 25 that the operator has placed a new test strip 16 in the loading area 38. In this case, the loading area sensor 42 couples to the processor 25 by a control line 43. Upon receiving the loading area sensor signal from the loading area sensor 42, the processor 25 uses the timing mechanism to keep track of an elapsed time from the placement of the corresponding test strip 16 on the loading area 38 as described above. The loading area sensor 42 can include an optical interrupter utilizing a modulated LED 44 and a synchronous photodetector 46. When a test strip 16 is placed on the loading area 38, a beam from the LED 44 is broken, and the photodetector 46 detecting the corresponding signal change, triggers the loading area sensor signal from the loading area sensor 42 to the processor 25. Other apparatus or methods of detecting test strip placement are possible, such as motion detection by reflection of infrared light or ultrasonic pulses or detection of capacitance changes. In the embodiment of FIG. 2, this same loading area sensor signal also triggers the transport mechanism 36 to move the test strip 16 in the viewing field 14 either directly through a control line coupling the loading area sensor 42 to the transport mechanism 36 or indirectly through a control line coupling the processor 25 to the transport mechanism 36.

The transport mechanism 36 includes a motor control circuitry 49 that controls the operation of a motor 50. The motor control circuitry 49 is coupled to the motor 50 and can vary widely in form depending on the embodiment. The motor control circuitry 49 can be coupled directly to the loading area sensor 42, the processor 25 or both depending on the embodiment. If an embodiment utilizes processor 25 to determine the placement of a test strip 16 on the loading area and not a loading sensor, then the motor control circuitry 49 couples to the processor 25 through a control line. But if the loading area sensor 42 detects new strip placement as in FIG. 2, the motor control circuitry 49 can couple to the loading area sensor 42 through a control line 45 in order to receive loading area sensor signals. The motor control circuitry 49 can alternatively couple to the processor 25 through a control line 47 to receive motor control signals from the processor 25 after the processor 25 receives a loading area sensor signal. FIG. 2 shows both the processor 25 and the loading sensor 42 coupled to the motor control circuitry 25, so both can signal the motor control circuitry 49.

In FIG. 2, the transport mechanism 36 further includes the motor 50, a strip conveyor 48, a movement assembly 53, such as a conventional Geneva assembly 53, and a blotter arm 51. The motor 50 provides the power to mechanically operate the transport mechanism 36. The motor 50 is mechanically linked to the Geneva assembly 53. The Geneva assembly 53 is mechanically linked in a timed relation to the strip conveyor 48 and the blotter arm 51 to coordinate the movement of both the strip conveyor 48 and the blotter arm 51 according to the characteristics of the Geneva assembly 53. The coordinated movement of the strip conveyor 48 and the blotter arm 51 efficiently indexes the test strips 16 onto the strip conveyor 48 as described below.

FIG. 2 shows the blotter arm 51 on the loading area 38. Whenever a test strip 16 is placed onto the loading area 38, the motor control circuitry 49 receives a signal from either the processor 25 or the loading area sensor 42. The motor control circuitry 49 activates motor 50 causing the blotter arm 51 to move the test strip 16 onto the strip conveyer 48. The test strip 16 does not move on the strip conveyor 48 until another test strip is placed in the loading area 38. At that time, the blotter arm 51 moves the next test strip onto the strip conveyor 48 while conveyor 48 moves the test strip 16 a fixed distance. Each test strip 16 in the viewing field 14 will move the same fixed distance with each subsequent index of another test strip. This calibrated and intermittent movement permits the proper indexing of test strips and is accomplished with the Geneva assembly 53. Consequently, the transport mechanism 36 indexes multiple test strips 16 in the viewing field 14 and, thereby, maximizes the number of test strips 16 in the viewing field 14 and improves the efficiency of the video strip reader 11.

Figure 3:
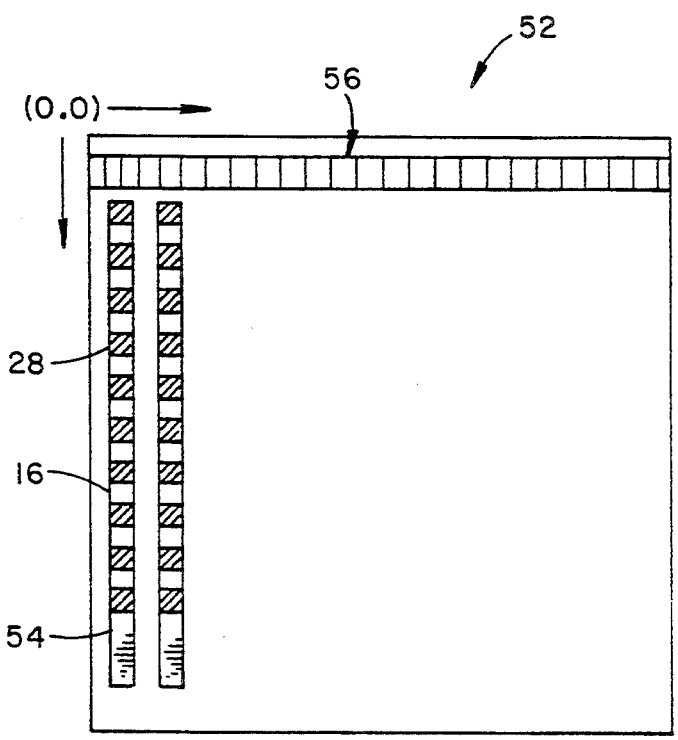
FIG. 3 shows an image of the viewing area with two strips and a color standard thereon.

FIG. 3 shows an image 52 of the viewing field 14. The image 52 is composed of a two-dimensional array of pixels representing the viewing field 14. The upper left hand corner of the image 52 represents the origin of this two-dimensional array with coordinates (0,0) in pixels. The x-axis pixel coordinates increase by moving horizontally from left to right across the image 52 along a horizontal line of pixels, and the y-axis pixel coordinates increase vertically from top to bottom along a vertical column of pixels. Each pixel contains color information broken down into red, green or blue (RGB). The processor 25 analyzes the image 52 to determine the location and orientation of the test strip 16 and its test pads 28. When the elapsed time for the test strip 16 exceeds an incubation time for a test pad 28 on that test strip 16, the processor 25 measures the reflectance for that portion of the two dimensional pixel array or image 52 representing that test area or test pad 28. This step is repeated for multiple read times. The processor 25 then calculates the concentration of the constituents of interest in the specimen or other test results.

Because of its video imaging capabilities, the present invention can utilize markings 54 incorporated on each test strip 16 to distinguish between individual test strips and different types of test strips. By utilizing a patient or sample ID on each test strip 16, the present invention can evaluate the alphanumeric or bar code information and report the results for each specimen or patient, reducing the possibility of human recording error. In addition, the ability to distinguish between different types of test strips enhances the flexibility of the present invention because the present invention can alter its analysis or timing to accommodate for the different type of test strip 16.

The video strip reader of the present invention can also utilize a color standard 56 contained in the viewing field to ensure that the present invention accurately analyzes the test strips. FIG. 3 illustrates a color standard 56 on the image 52 in the form of a color strip. By having a color standard 56 on the viewing field, an absolute reflectance standard is always present for the processor 25 when analyzing the image 52. The color standard 56 permits continuous correction for illumination changes. Alternatively, the color standard 56 can be located on the test strip itself.

Figure 4:
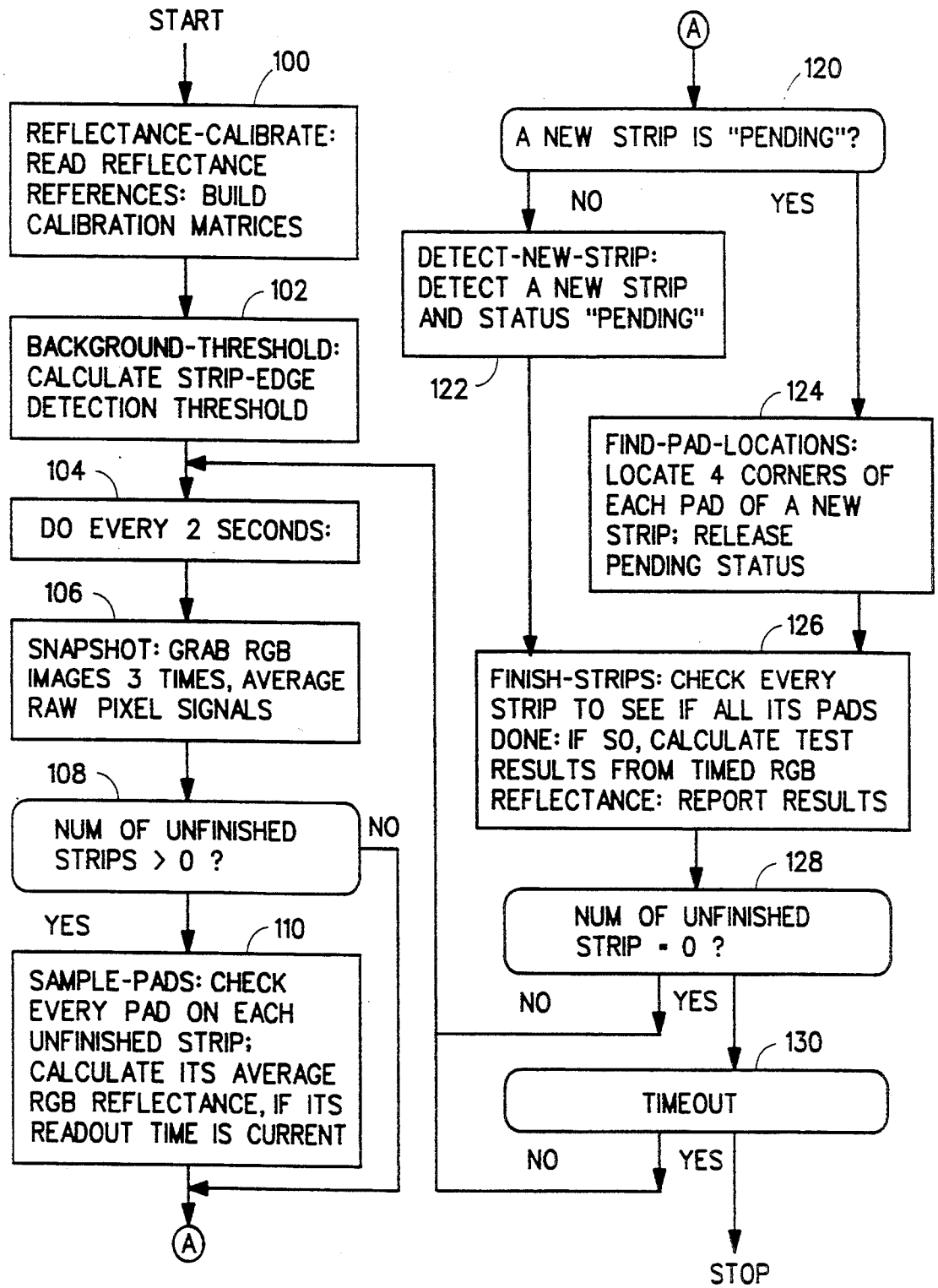
FIG. 4 is a flow chart diagram illustrating the operation of the video test strip reader in accordance with the present invention.

FIG. 4 is a flow chart diagram of the overall operation of the embodiment illustrated in FIG. 1. Initially, step 100 calibrates the reflectance for the video strip reader 10. The processor 24 builds RGB reflectance reference matrices or calibration matrices for the viewing field 14 by reading the red, green and blue reflectance values for the viewing field 14. Step 102 calculates a background threshold for reflectance from the blue reflectance reference matrix. The processor 24 rejects any reflectance values below the background threshold as noise, but reflectance values above the background threshold can represent the presence of a test strip 16 on the viewing field 14. Step 104 sets a loop in which processor 24 cycles through steps 106–128 about every two seconds when unfinished test strips are present on the viewing field 14. Step 106 creates raw reflectance matrices for the red, green and blue colors (RGB) of the image 52 by grabbing the RGB image 52 three times and averaging the raw pixel signals to complete the raw RGB reflectance matrices. Step 108 determines whether there are unfinished test strips on the viewing field 14. If not, the processor 24 proceeds to step 122 to detect any new test strips and classify any new test strips as "pending."

If unfinished test strips exist, the processor 24 performs step 110 by checking every test pad 28 on each unfinished test strip. Step 110 calculates the RGB reflectance values for each test pad with a current read time. Next, step 120 checks if a new test strip is "pending." If no new test strip is "pending," the processor proceeds to step 122 to detect any new test strips and classify any new strips as "pending." If a "pending" new test strip exists, step 124 finds the location for each test pad 28 by locating the four corners of each test pad 28 of a "pending" new test strip and releases the "pending" status of the new test strip.

After labeling any new test strips as "pending" or locating the test pads 28 for a previously "pending" test strip, the present invention checks all test strips to determine whether a test strip is finished. A test strip 16 is finished when the read time or times for every test pad 28 on the test strip 16 has expired and the RGB reflectance values for every test pad 28 on the finished test strip was determined at step 110. If a test strip 16 is finished, step 126 reports the test results derived from the timed RGB reflectance values for that test strip 16. Finally, step 128 determines whether any unfinished strips remain. If so, the processor 24 cycles back to step 104, grabs a new set of RGB images, averages the raw pixel signals to construct another set of raw RGB reflectance matrices, and proceeds through the steps 106–128.

The processor 24 performs an operation cycle every two seconds at step 104. If all strips are finished, step 130 determines whether a predetermined amount of time has passed since a new test strip has been placed onto the viewing field 14. If the time limit has expired, the illustrative system stops, but if the time limit is not exceeded, the processor 24 continues cycling through steps 106–130 every two seconds.

Figure 5:
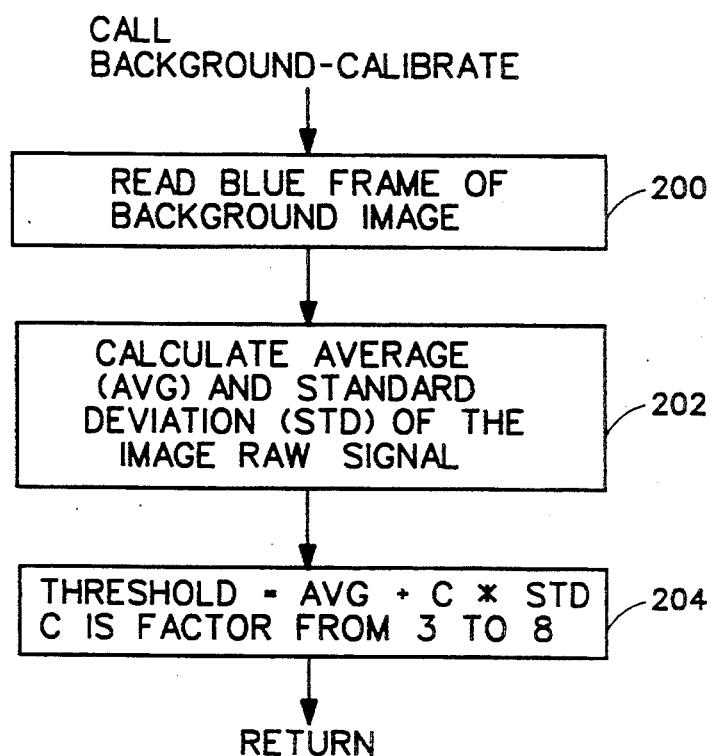
FIGS. 5–10 are flow chart diagrams detailing the individual operations illustrated in FIG. 4.

FIG. 5 details how step 102 of FIG. 4 calculates the background threshold level for a background image in order to accomplish strip-edge detection of steps 122 and 124. Initially, step 200 grabs the blue reflectance reference matrix of the background image created at step 100 of FIG. 4. Step 202 calculates the average blue reflectance value for the background image using the blue reflectance reference matrix as well as the standard deviation. Step 204 determines the background threshold level with the equation:

$$\text{THRESHOLD} = \text{AVERAGE} + C * \text{STANDARD DEVIATION},$$

where C is a factor from 3 to 8.

Figure 6:
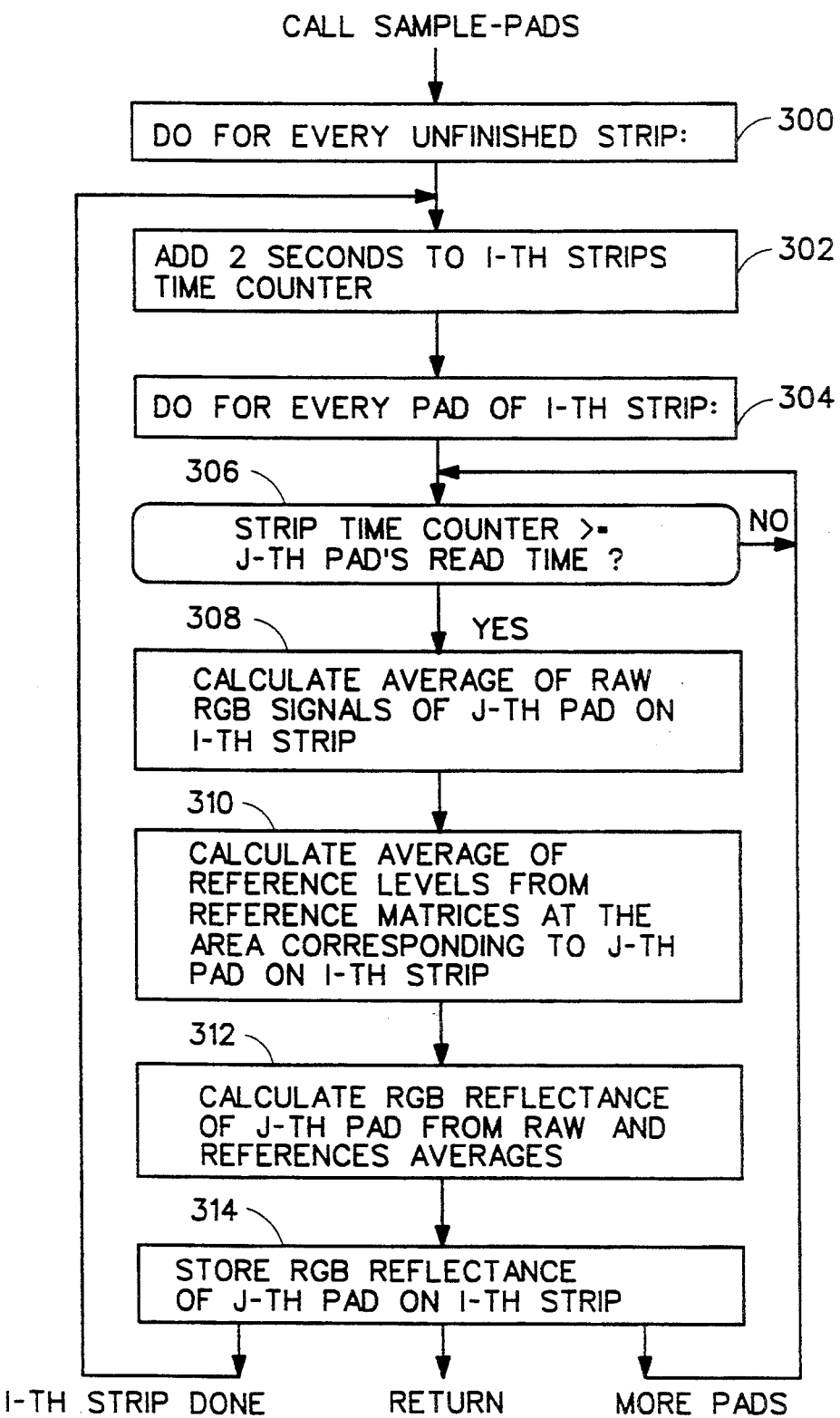

After the present invention determines that unfinished test strips exist at step 108 of FIG. 4, step 110 of FIG. 4 checks every test pad on each unfinished test strip and calculates its RGB reflectance if the read time for the test pad has expired. FIG. 6 details the operation of step 110 of FIG. 4. Step 300 establishes an unfinished test strip loop based on the number of unfinished test strips. Step 302 adds two seconds to the time counter for an I-th unfinished test strip within the unfinished test strip loop of step 300. Step 304 establishes a test pad loop within the unfinished test strip loop based on the number of test pads for the I-th unfinished test strip. For a J-th test pad on the I-th unfinished test strip, step 306 determines whether the time counter or current time for the I-th unfinished test strip equals or exceeds the read time for the J-th test pad. If not, the processor 24 advances the test pad loop to the next test pad on the I-th unfinished test strip and proceeds back to step 306.

If step 306 determines that the read time of the J-th test pad on the I-th test strip has expired, the processor 24 must calculate the RGB reflectance values for the J-th pad. First, step 308 calculates an average raw RGB reflectance for the J-th test pad on the I-th test strip. Next, for the area corresponding to the J-th test pad on the I-th test strip, step 310 derives the average reflectance reference levels from the RGB reflectance reference matrices or calibration matrices of step 100. With the average reflectance reference levels and the average raw RGB reflectance corresponding to the J-th pad on the I-th strip, step 312 derives the RGB reflectance values for the J-th pad on the I-th strip. Step 314 stores the RGB reflectance values for the J-th pad on the I-th strip. If more test pads exist on the I-th test strip, processor 24 advances to the next test strip and proceeds to step 306. But if the test pad loop finishes, the processor 24 advances to the next test strip and proceeds to step 302. When the unfinished test strip loop finishes, the processor returns to step 120 of FIG. 4.

Figure 7:
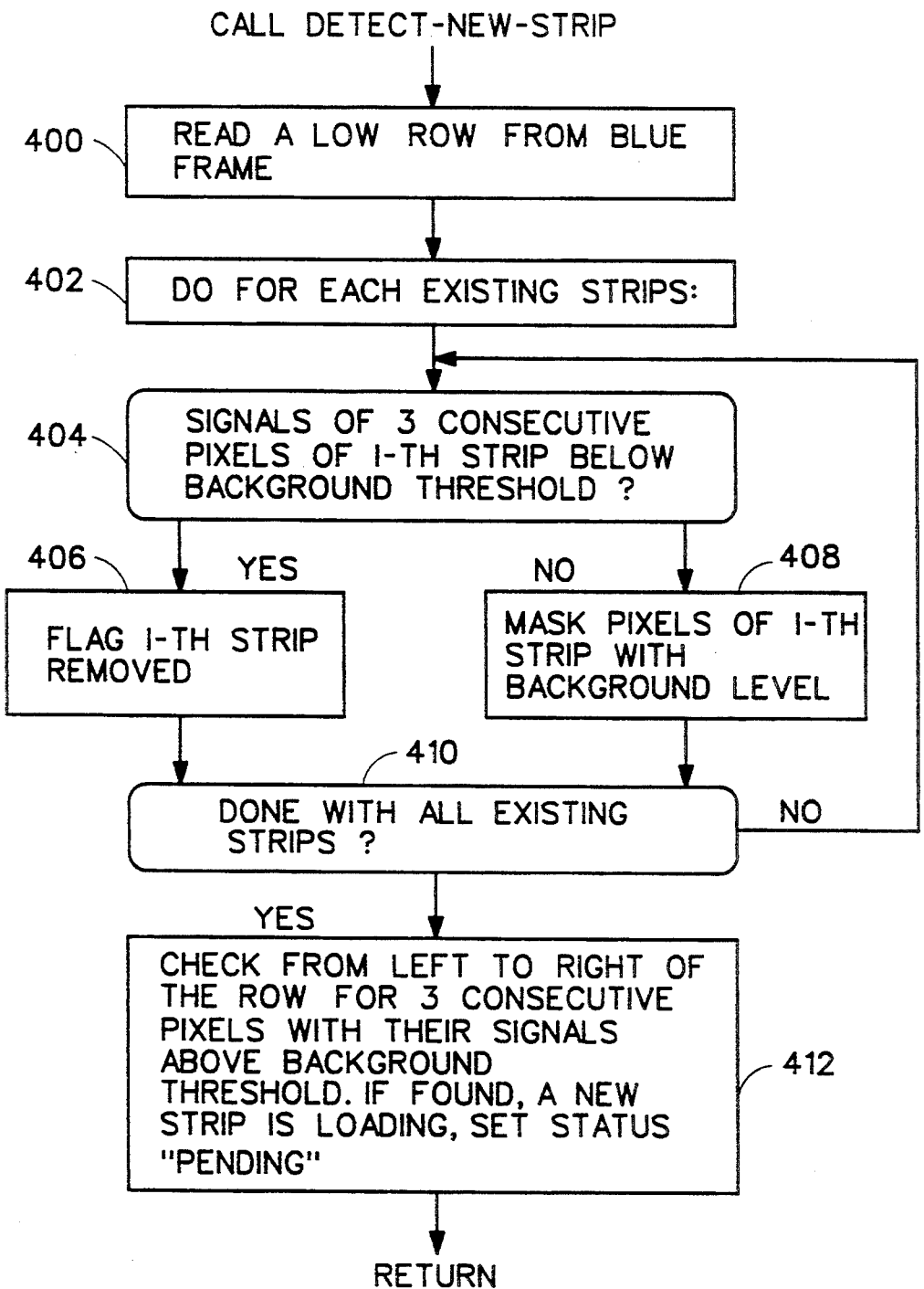

FIG. 7 details step 122 of FIG. 4 for detecting the presence of a new test strip on the viewing field. Step 400 begins by reading a predetermined low row from the raw blue reflectance matrix of the raw RGB reflectance matrices of step 106. Step 402 establishes an existing test strip loop. For each existing I-th test strip within the existing test strip loop, step 404 determines whether three consecutive pixels of the existing I-th test strip are below the background threshold level calculated in FIG. 5. If the three consecutive pixels of the existing I-th strip are below the background threshold level, then step 406 recognizes that the existing I-th test strip has been removed from the viewing field 14. But if the three consecutive pixels of the existing I-th test strip remain above the background threshold level, step 408 recognizes that the existing I-th test strip remains on the viewing field 14, and step 408 masks the pixels of the existing I-th test strip with the background threshold level.

After the processor 24 determines the status of all existing test strips and masks those pixels on the low row corresponding to existing test strips, processor 24 proceeds from step 410 to step 412. Step 412 detects the presence of new test strips by checking from left to right on the low row for three consecutive pixels above the background threshold value (three consecutive pixels were chosen only to provide good "noise" immunity), signalling the edge of a new test strip on the viewing field 14. Step 412 sets the status of any new test strip as "pending" and returns the processor 24 to step 126 of FIG. 1.

If, at step 120, the processor 24 determines that a new strip is "pending" from the previous cycle through the new strip detection mechanism of FIG. 7, step 124 locates the four corners of each pad of a new strip and releases the "pending" status for a new test strip.

Figure 8:
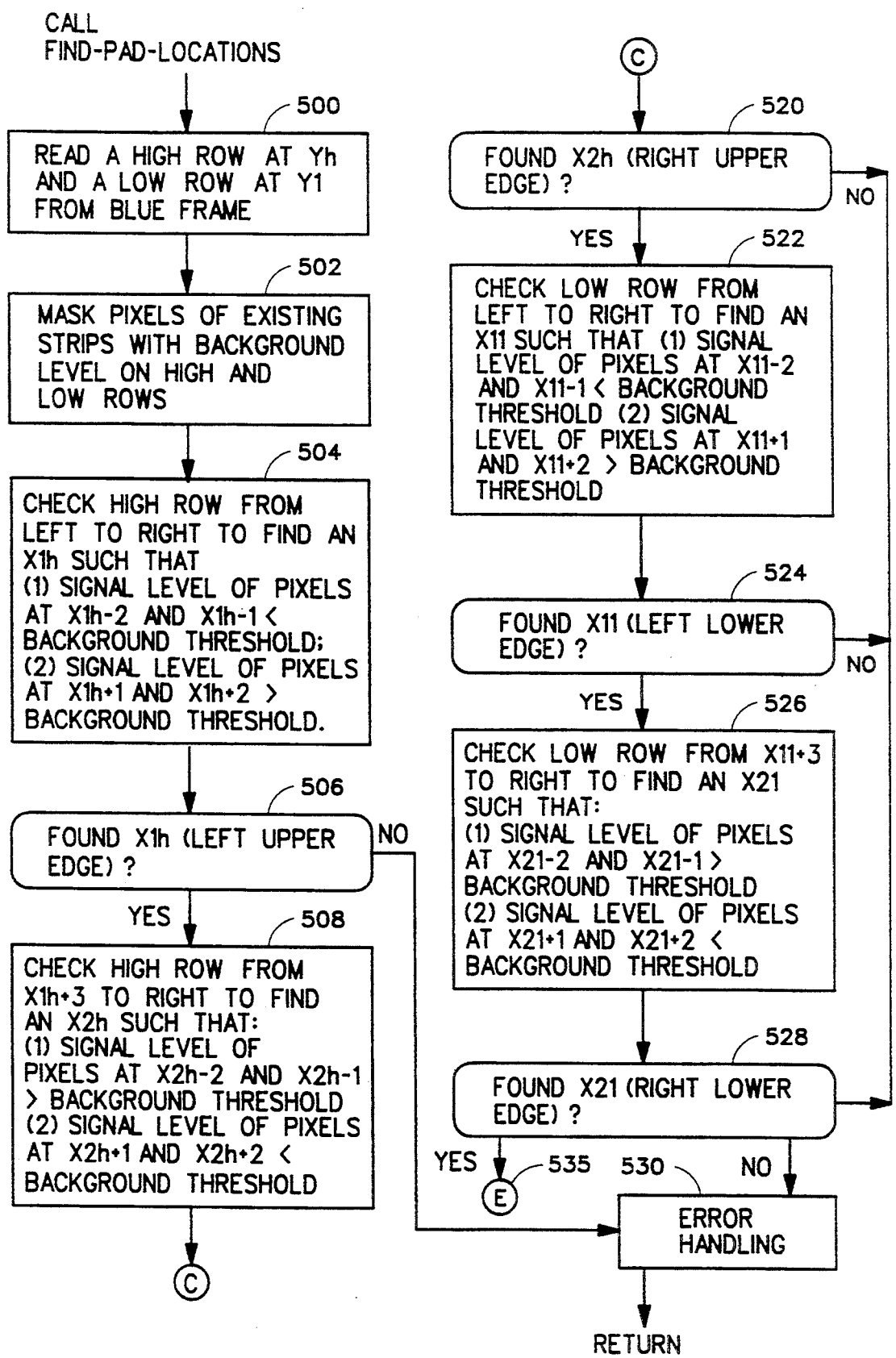

FIG. 8 details an initial portion of step 124 in which processor 24 finds four boundary points for a "pending" new test strip. Step 500 reads a high row (Yh) and a low row (Yl) from the raw blue reflectance matrix of step 106. On those high and low rows selected by step 500, step 502 masks pixels of existing test strips with the background level. Step 504 finds the left upper edge boundary point, X1h, of the "pending" new test strip by checking the high row from left to right to find the X1h that marks the boundary point between the background of the viewing field 14 and the "pending" new strip. Step 504 determines X1h by finding the point along tile high row, Yh, where the pixel values at X1h−2 and X1h−1 are less than the background threshold level and the pixel values at X1h+1 and X1h+2 are greater than the background threshold level.

After finding the left upper edge point, X1h, of the "pending" new strip at step 504, the processor 24 locates the right upper edge boundary point, X2h, for the "pending" new test strip at step 508. Step 508 finds X2h by checking the high row Yh to the right of X1h+3 and finding the point where the pixel values at X2h−2 and X2h−1 are greater than the background threshold level and the pixel values at X2h+1 and X2h+2 are less than the background threshold level. If either X1h or X2h is not found, processor 24 proceeds to step 530 to determine where the error occurred because any "pending" new strip must have these upper boundary points.

Similarly, processor 24 then locates the lower edge boundary points for a "pending" new test strip. Step 522 finds the left lower edge boundary point, X1l, along the low row, Yl, of step 500. Step 522 searches for X1l along the low row such that the pixel values at X1l−2 and X1l−1 are less than the background threshold level and the pixel values at X1l+1 and X1l+2 are greater than the background threshold value. Finally, step 526 locates the right lower edge boundary point, X2l, along Yl for the "pending" new test strip. Step 526 finds X2l as the point along Yl where the pixel values at X2l−2 and X2l−1 are greater than the background threshold level and the pixel values at X2l+1 and X2l+2 are less than the background threshold level. Step 524 or step 528 directs processor 24 to a error handing step 530 if processor 24 fails to find either lower edge boundary points, X1l or X2l.

Figure 9:
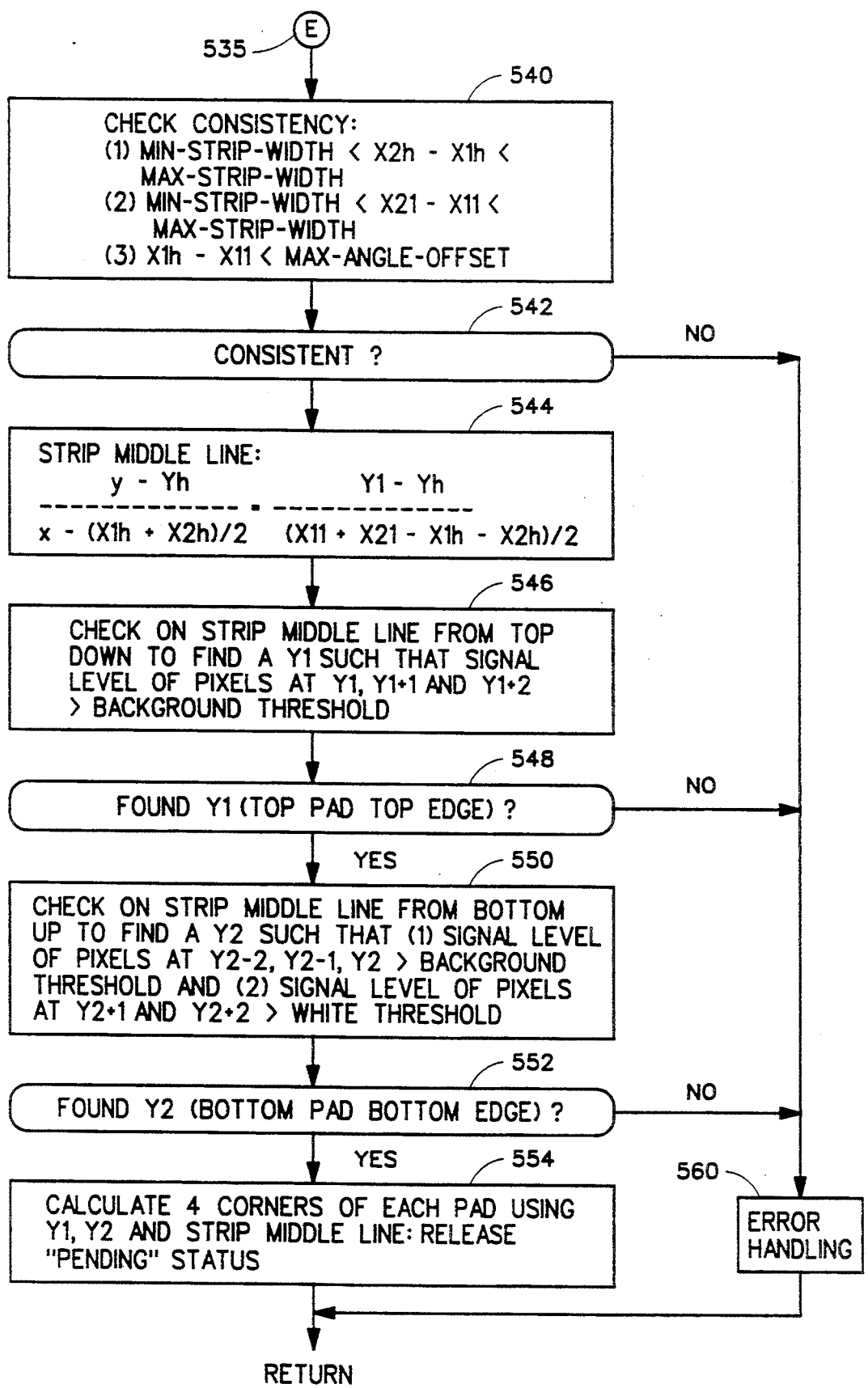

Upon reaching connector 535, processor 24 has located the two upper edge boundary points along high row, Yh, and the two lower edge boundary points along low row, Yl. FIG. 9 shows how processor 24 takes the four edge boundary points and determines the test pad locations for a "pending" new test strip from these four edge boundary points. Step 540 ensures that the four edge boundary points are reasonable by checking the consistency of the four edge boundary points against values representing the minimum test strip width (MIN_STRIP_WIDTH), the maximum test strip width (MAX_STRIP_WIDTH) and the maximum angle offset (MAX_ANGLE_OFFSET). Step 540 checks if:

1) MIN_STRIP_WIDTH < X2h − X1h < MAX_STRIP_WIDTH;
2) MIN_STRIP_WIDTH < X2l − X1l < MAX_STRIP_WIDTH; and
3) X1h − X1l < MAX_ANGLE_OFFSET. If the four edge boundary points are not consistent with a test strip 16, step 542 directs the processor 24 to an error handing step 560. But if the four edge boundary points are consistent with a test strip 16, step 544 finds a middle line for the "pending" new strip. Step 544 derives the middle line equation for the new test strip with the following proportion:

$$\frac{y - Yh}{x - (X1h + X2h)/2} = \frac{Yl - Yh}{(X1l + X2l - X1h - X2h)/2}.$$

Step 546 finds the top edge of the top test pad on the test strip. Step 546 checks along the middle line from the top and searches for a Y1 where the pixel values at Y1, Y1+1 and Y1+2 are greater than the background threshold value. According to the MULTISTIX® reagent test strips currently used, the top edge of the top test pad forms the top edge of the test strip itself as shown in FIG. 3. If a top edge is not found, step 548 directs processor 24 to the error handling step 560. If step 546 finds a top edge for the top test pad, step 550 finds the bottom edge of the bottom test pad. Step 550 searches along the middle line from the bottom for a Y2 such that the pixel values at Y2−2, Y2−1 and Y2 are greater than the background threshold level and pixel values at Y2+1 and Y2+2 are greater than a white background threshold level. If a bottom edge is not found, step 552 directs the processor 24 to the error handling step 560. Otherwise, step 554 calculates the four corners for each test pad using Y1, Y2, the middle line for the test strip and the known test pad characteristics for the test strip 16. Finally, step 554 releases the "pending" status for the test strip 16.

Figure 10:
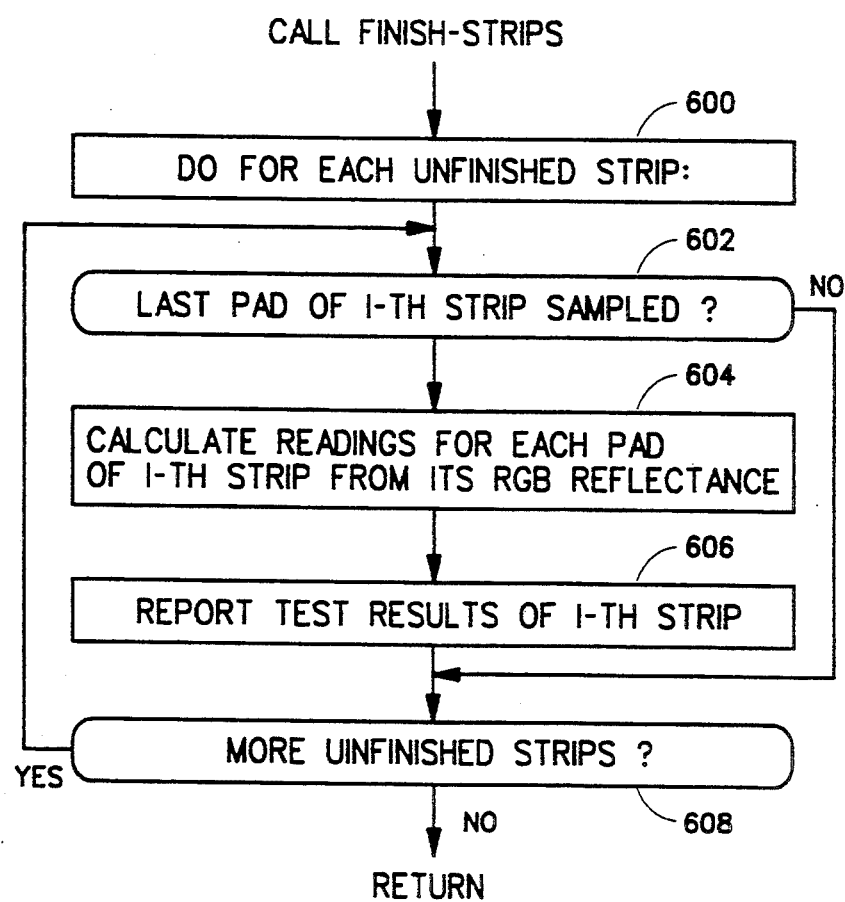

After completing either step 122 or step 124 of FIG. 4, processor 24 proceeds to step 126 in order to finish unfinished test strips. FIG. 10 details step 126 of FIG. 4. Step 600 establishes a loop based on the number of unfinished test strips. For each I-th unfinished test strip within the unfinished test strip loop, step 602 determines whether the processor 24 has sampled final timed RGB reflectance values of the last pad on the I-th unfinished test strip. If not, the test pad remains unfinished, and the processor 24 moves to the next unfinished test strip. If the processor 24 has sampled the last pad, then the test strip 16 is finished, and step 604 calculates the readings for each pad 28 of the test strip 16 using the timed RGB reflectance values for that test pad 28. After calculating the readings for the finished test pad, step 606 reports the test results for the finished test strip.

The present invention has been described as using a color CCD camera. The present invention, however, can employ a monochrome camera using color filters. Typically, the monochrome camera has a higher resolution than color cameras and the use of the monochrome camera arrangement can be advantageous. Also, the present invention is described as scanning the blue matrix of the raw RGB reflectance matrices to detect a new test strip and the RGB reflectance reference matrices to locate the pads on a "pending" new strip. The present invention, however, encompasses scanning any color matrix to perform these functions. Additionally, the present invention also encompasses constructing new RGB reflectance reference matrices or calibration matrices periodically in order to provide updated RGB reflectance reference matrices.

Thus, the video test strip reader and method of the present invention and many of its attendant advantages will be understood from the foregoing description and various modifications may be made in the form, construction and arrangement of the parts thereof without departing from the spirit and scope of the invention or sacrificing all of its material advantages, the form described above being merely a preferred embodiment thereof.

We claim:

1. A video test strip reader for reading reagent test strips, said test strips each having test pads, each of said test pads reacting with a sample when contacting said sample and changing color according to one or more read times for each of said test pads and an amount of a constituent or property in said sample, comprising:
   a video imager adjacent to a viewing area for converting an image of said viewing area to an analog signal representing said image;
   a signal converter responsive to said analog signal, said signal converter converting said analog signal into a digital signal representing said image;
   an image handler responsive to said digital signal, said image handler storing said image represented by said digital signal; and
   a processor coupled to said image handler for analyzing said image to determine a placement of a test strip at any location on said viewing area, said processor determining the location and orientation of a test strip on said viewing area and identifying a test pad for said test strip, said processor including a timing mechanism for tracking an elapsed time from said placement of each of said test strips, said processor analyzing a portion of said image representing an identified test pad of said test strip after said read times for said test pad, said processor calculating said amount of said constituent or property in said sample from said analysis of said portion of said image.

2. The video reader of claim 1 further comprising a transport mechanism with at least a portion of said transport mechanism being in said viewing field, said transport mechanism transporting said test strips across said viewing field.

3. The video test strip reader of claim 1 wherein said video imager is a color camera.

4. The video test strip reader of claim 1 wherein said video imager is a monochrome camera having a plurality of color filters.

5. The video test strip reader of claim 3 or 4 wherein said image handler is a frame-grabber board.

6. The video test strip reader of claim 5 wherein said processor includes a conventional personal computer, said frame-grabber board coupled to an I/O port of said personal computer.

7. The video test strip reader of claim 1 wherein said video imager includes said signal converter.

8. The video test strip reader of claim 1 wherein said image handler includes said signal converter.

9. The video test strip reader of claim 1 wherein said processor is a DSP processor on a dedicated board.

10. The video test strip reader of claim 1 further comprising an illumination source illuminating said viewing area.

11. The video test strip reader of claim 1 further comprising a storage memory coupled to said processor, said processor storing reference values in said storage memory, said processor using said reference values to calibrate said video test strip reader and compensate for any illumination variations on the viewing area.

12. The video test strip reader of claim 1 further comprising a displayer coupled to said processor.

13. A video test strip reader for reading reagent test strips, said test strips each having test pads, each of said test pads reacting with a sample when contacting said sample and changing color in proportion with one or more read times for each of said test pads and an amount of a constituent or property in said sample, comprising:
   a video imager adjacent to a viewing area for converting an image of said viewing area to an analog signal representing said image;
   a signal converter responsive to said analog signal, said signal converter converting said analog signal into a digital signal representing said image;
   an image handler responsive to said digital signal, said image handler storing said image represented by said digital signal;
   a transport mechanism with at least a portion of said transport mechanism being in said viewing area, said transport mechanism receiving said test strips and transporting said test strips across said viewing area; and
   a processor coupled to said image handler for analyzing said image to determine a location and orientation for a test strip placed at any location on said viewing area, said processor identifying a test pad relative to said location and orientation for said test strip, said processor including a timing mechanism for tracking an elapsed time from the placement of said test strip, said processor analyzing a portion of said image representing a test pad of said test strip after said read time for said test pad, said processor calculating said amount of said constituent in said sample from said analysis of said portion of said image.

14. The video test strip reader of claim 13 wherein said transport mechanism has a loading end and a waste end, said viewing area is between said loading end and said waste end, said transport mechanism receives said test strips at said loading end, said transport mechanism transports said test strips across said viewing area for analysis and deposits said test strips in a waste receptacle at said waste end.

15. The video test strip reader of claim 14 further comprising a loading sensor at said loading end of said transport mechanism, said loading sensor signalling said processor that said transport mechanism has received said test strip, said processor triggering said timing mechanism for said test strip upon receiving said signal.

16. The video test strip reader of claim 15 wherein said loading sensor includes an optical interrupter utilizing a modulated light source and a synchronous photodetector such that said light source shines a light beam across said loading end of said transport mechanism directly at said photodetector, said light beam is broken upon said transport mechanism receiving said test strip, said loading sensor signals said processor upon receiving said test strip.

17. The video test strip reader of claim 13 wherein said video imager is a color camera.

18. The video test strip reader of claim 13 wherein said video imager is a monochrome camera having a plurality of color filters.

19. The video test strip reader of claim 17 or 18 wherein said image handler is a frame-grabber board.

20. The video test strip reader of claim 19 wherein said processor includes a conventional personal computer, said frame-grabber board is coupled to an I/O port of said personal computer.

21. The video test strip reader of claim 13 wherein said video imager includes said signal converter.

22. The video test strip reader of claim 13 wherein said image handler includes said signal converter.

23. The video test strip reader of claim 13 wherein said processor is a DSP processor on a dedicated board.

24. The video test strip reader of claim 13 further comprising an illumination source illuminating said viewing area.

25. The video test strip reader of claim 13 further comprising a storage memory coupled to said processor, said processor storing reference values in said storage memory, said processor using said reference values to calibrate said video test strip reader and compensate for any illumination variations on the viewing area.

26. The video test strip reader of claim 13 further comprising a displayer coupled to said processor.

27. A video test strip analyzer for analyzing an image represented by a digital signal, said image being of a viewing field with reagent test strips, said test strips each having test pads, each of said test pads reacting with a sample when contacting said sample and changing color according to one or more read times for each of said test pads and an amount of a constituent or property in said sample, comprising a processor analyzing said image to determine a location and orientation for a test strip placed at any location on said viewing area, said processor identifying a test pad for said test strip, said processor including a timing mechanism for tracking an elapsed time from said placement of said test strip, said processor analyzing a portion of said image representing a test pad of said test strip after said read times for said test pad, said processor calculating said amount of said constituent or property in said sample from said analysis of said portion of said image.

28. The video test strip analyzer of claim 27 wherein said processor includes a conventional personal computer.

29. The video test strip analyzer of claim 27 wherein said processor is a DSP processor on a dedicated board.

30. The video test strip analyzer of claim 27 further comprising a storage memory coupled to said processor, said processor storing reference values in said storage memory, said processor using said reference values to calibrate said video test strip reader and compensate for any illumination variations on the viewing area.

31. The video test strip analyzer of claim 27 further comprising a displayer coupled to said processor.

32. A method for reading reagent test strips each having test pads, each of said test pads reacting with a sample when contacting said sample and changing color in proportion to one or more read times for each of said test pads and an amount of a constituent or property in said sample, comprising the steps of:

converting an image of a viewing area into a digital signal representing said image;

storing said digital signal representing said image;

detecting a test strip placed at any location on said viewing area by analyzing said digital signal representing said image;

determining the location and orientation of said test strip on said image;

identifying portions of said image representing a test pad on said test strip;

timing said test strip starting at said detection of said test strip to obtain a current time for said test strip;

determining whether said read time for said test pad has expired by comparing said read time with the current time for said test strip;

analyzing said portion of said image representing said expired test pad to obtain a raw reflectance value for a portion of said image representing said expired test pad; and calculating said mount of said constituent or property in said sample from said raw reflectance value for said portion of said image representing said expired test pad.

33. The method of claim 32 further comprising the initial steps of:

converting a reflectance reference image into a digital signal;

storing said digital signal in reflectance reference matrices; and obtaining a threshold signal level from said reflectance reference matrices.

34. The method of claim 33 wherein said step of calculating further comprises compensating said raw reflectance value with said reflectance reference matrices to correct illumination variations on said viewing area and to obtain a reflectance value for said expired test pad.

35. The method of claim 32 further comprising the step of transporting said test strip across said viewing field.

36. The method of claim 32 further comprising the step of displaying results from said calculation.

37. The method of claim 32 wherein said steps following said step of converting further comprise employing a conventional personal computer.

38. The method of claim 32 wherein said steps following said step of converting further comprise employing a DSP processor on a dedicated board.

39. The method of claim 32 further comprising the step of illuminating said viewing area.

40. A method for reading reagent test strips each having test pads, each of said test pads reacting with a sample when contacting said sample and changing color according to one or more read times for each of said test pads and an amount of a constituent or property in said sample, comprising the steps of:

receiving a test strip;

transporting said test strip across a viewing area;

converting an image of said viewing area into a digital signal representing said image;

storing said digital signal representing said image;

determining a location and orientation for said test strip at any location on said viewing area by analyzing said image represented by said digital signal;

identifying portions of said image relative to said location and orientation representing a test pad on said test strip;

timing said test strip starting at said receiving of said test strip to obtain a current time for said test strip;

determining whether said read time for said test pads of said test strip has expired by comparing said read time with said current time for said test strip;

analyzing a portion of said image representing said expired test pad to obtain a raw reflectance value for said portion of said image representing said expired test pad: and calculating said amount of said constituent or property in said sample from said raw reflectance value for said portion of said image representing said expired test pad.

41. The method of claim 40 further comprising the initial steps of:

converting a reflectance reference image into a digital signal;

storing said digital signal in reflectance reference matrices; and obtaining a threshold signal level from said reflectance reference matrices.

42. The method of claim 41 wherein said step of calculating further comprises compensating said raw reflectance value with said reflectance reference matrices to correct illumination variations on said viewing area and to obtain a reflectance value for said expired test pad.

43. The method of claim 40 wherein said step of receiving further comprises receiving said test strip at a loading end of a transport mechanism.

44. The method of claim 40 further comprising the step of depositing said test strips in a waste receptacle at said waste end of said transport mechanism.

45. The method of claim 43 wherein said step of receiving further comprises the steps of:

employing a loading sensor at said loading end of said transport mechanism for detecting said receiving said test strip;

providing a signal that said transport mechanism has received said test strip; and triggering a timing mechanism with said signal for said test strip.

46. The method of claim 45 further comprising the steps of:

employing an optical interrupter utilizing a modulated light source and a synchronous photodetector such that said light source shines a light beam across said loading end of said transport mechanism directly at said photodetector as said loading sensor: and providing said signal upon said light beam being broken.

47. The method of claim 40 wherein said step of converting further comprises the step of employing a color camera.

48. The method of claim 40 wherein said step of converting further comprises the step of employing a monochrome camera having a plurality of color filters.

49. The method of claim 40 wherein said steps following said step of converting further comprise the step of employing a conventional personal computer.

50. The method of claim 40 further comprising the step of displaying results from said calculation.

51. The method of claim 40 wherein said steps following said step of converting further comprise employing a conventional personal computer.

52. The method of claim 40 wherein said steps following said step of converting further comprise employing a DSP processor on a dedicated board.

53. The method of claim 40 further comprising the step of illuminating said viewing area.

54. A method for analyzing an image represented by a digital signal, said image being of a viewing field with reagent test strips each having test pads, each of said test pads reacting with a sample when contacting said sample and changing color according to one or more read times for each of said test pads and an amount of a constituent or property in said sample, comprising the steps of:

determining a location and orientation of a test strip placed at any location on said viewing field;

identifying portions of said image representing a test pad on said test strip;

timing said test strip to obtain a current time for said test strip;

determining whether said read time for said test pad on said test strip has expired by comparing said read time with the current time for said test strip;

analyzing said portion of said image representing said expired test pad to obtain a raw reflectance value for a portion of said image representing said expired test pad; and calculating said amount of said constituent or property in said sample from said raw reflectance value for said portion of said imaging representing said expired test pad.

55. The method of claim 54 further comprising the initial steps of:

constructing reflectance reference matrices from a digital signal representing a reflectance reference image; and obtaining a threshold signal level from said reflectance reference matrices.

56. The method of claim 55 wherein said step of calculating further comprises compensating said raw reflectance value with said reflectance reference matrices to correct illumination variations on said viewing area and to obtain a reflectance value for said expired test pad.

57. The method of claim 54 further comprising the step of outputting said results from said calculation.

58. The method of claim 54 further comprising employing a conventional personal computer.

59. The method of claim 54 further comprising employing a DSP processor on a dedicated board.

* * * * *